United States Patent [19]

Shiraki et al.

[11] 4,243,636
[45] Jan. 6, 1981

[54] APPARATUS FOR THE CONTINUOUS LIQUID-PHASE CATALYTIC OXIDATION OF ALKYL-SUBSTITUTED AROMATIC COMPOUNDS

[75] Inventors: Shigemi Shiraki, Iwakuni; Ryoichi Yamamoto, Yamaguchi, both of Japan

[73] Assignee: Mitsui Petrochemical Industries Ltd., Tokyo, Japan

[21] Appl. No.: 10,914

[22] Filed: Feb. 9, 1979

[30] Foreign Application Priority Data

Feb. 15, 1978 [JP] Japan .................................. 53/15335

[51] Int. Cl.³ .......................... B01F 7/16; B01J 19/18; C07C 51/16
[52] U.S. Cl. .................................... 422/225; 366/101; 366/306; 366/328; 422/135; 422/193; 422/195; 422/226; 422/228; 562/416
[58] Field of Search ............... 422/135, 225, 226, 228, 422/231, 195, 193; 366/306, 325, 326, 328, 101, 107; 562/416, 412 (U.S. only), 413, 414

[56] References Cited

U.S. PATENT DOCUMENTS

| 1,781,435 | 11/1930 | Carper | 366/325 X |
|---|---|---|---|
| 1,870,980 | 8/1932 | Altwegg | 422/225 X |
| 2,075,070 | 3/1937 | Upton | 366/325 X |
| 2,191,830 | 2/1940 | Leedy | 366/325 X |
| 2,257,533 | 9/1941 | Reich | 422/225 X |
| 3,130,015 | 4/1964 | Monroe | 422/226 |
| 3,174,830 | 3/1965 | Watzl et al. | 422/135 |
| 3,839,435 | 10/1974 | Shigeyasu et al. | 422/225 X |
| 3,845,939 | 11/1974 | Waldenville | 422/225 X |
| 4,062,654 | 12/1977 | Shigeyasu et al. | 562/416 |
| 4,159,307 | 6/1979 | Shigeyasu et al. | 422/226 X |

*Primary Examiner*—Joseph Scovronek
*Attorney, Agent, or Firm*—Sherman & Shalloway

[57] ABSTRACT

In an apparatus for oxidizing an alkyl-substituted aromatic compound in the liquid phase with a molecular oxygen-containing gas in a lower aliphatic carboxylic acid solvent in the presence of an oxidation catalyst, said apparatus comprising a reaction vessel, a gas exhaust port at the top of the vessel, an inlet at the bottom of the vessel for feeding said molecular oxygen-containing gas, an inlet for feeding said solvent, an inlet for feeding said catalyst, an inlet for feeding said alkyl-substituted aromatic compound, an outlet for withdrawing the oxidation reaction product, and an agitator within the vessel, said agitator consisting of a rotating shaft provided along the axial direction of the vessel and a plurality of stages of agitating blades secured to said rotating shaft at spaced intervals; the improvement wherein at least one stage of agitating blades consists of comb-like flat blades each of which is composed of a plurality of comb tooth-like pieces aligned at spaced intervals.

11 Claims, 6 Drawing Figures

APPARATUS FOR THE CONTINUOUS LIQUID-PHASE CATALYTIC OXIDATION OF ALKYL-SUBSTITUTED AROMATIC COMPOUNDS

This invention relates to an apparatus for producing aromatic carboxylic acids having high purity and good color by the liquid-phase catalytic oxidation of alkyl-substituted aromatic compounds with a molecular oxygen-containing gas. The apparatus is simple in structure and easy to build, and can inhibit the undesirable oxidative decomposition of a lower aliphatic carboxylic acid solvent with reduced power consumption as compared with a conventional apparatus including an agitator equipped with an impeller composed of flat blades. Moreover, the apparatus of the invention can be built advantageously by replacing only the blade portion of the aforesaid conventional reaction apparatus.

It is the well-known commercial practice to produce aromatic carboxylic acids, for example terephthalic acid useful as a raw material for polyesters, by oxidizing alkyl substituted aromatic compounds such as p-xylene with a molecular oxygen-containing gas such as air in the liquid phase in a lower fatty acid carboxylic acid solvent such as acetic acid in the presence of a heavy metal oxidation catalyst such as a combination of a cobalt compound and a halogen compound.

It is also well known that to produce polyesters, such as polyethylene terephthalate, of high quality by a direct polymerization process, the starting terephthalic acid should be of high quality, and many suggestions have been made to produce such high-quality terephthalic acid by the commercially advantageous single-stage oxidation reaction of an alkyl-substituted aromatic compound. However, no entirely satisfactory improvement has yet been achieved to date.

In particular, the production by single-stage oxidation reaction of terephthalic acid having such a high quality as can be used in the direct polymerization process requires severe oxidation conditions which strictly limit the proportion and concentration of the solvent, the composition and concentration of the catalyst, the reaction temperature, the amount of the molecular oxygen-containing gas, and the residence time. If an attempt is made to produce high-quality terephthalic acid by catalytically oxidizing p-xylene in the liquid phase under these complex and disadvantageous controlled conditions, the oxidative decomposition of the acetic acid solvent increases greatly, and therefore, the use of such severe conditions does not provide a satisfactory means of producing high-quality terephthalic acid.

For this reason, the most common practice now in use for the production of such high-quality terephthalic acid, which is useful for producing a high-quality polyester such as polyethylene terephthalate by direct polymerization, is to use relatively mild oxidation conditions and to subject the resulting crude terephthalic acid containing fairly large amounts of impurities such as oxidation intermediates (e.g. 4-carboxybenzaldehyde) and coloring substances to a purifying treatment such as catalytic hydrogenation, catalytic decarbonylation or recrystallization. This process, however, is not entirely satisfactory for commercial practice because the treating operation requires installation of additional devices which are complex and expensive, and the cost of production necessarily increases.

One group of previous suggestions made to avoid the aforesaid disadvantages and troubles is directed to the improvement of the apparatuses themselves used for the liquid-phase catalytic oxidation of alkyl-substituted aromatic compounds with molecular oxygen-containing gases.

For example, Japanese Patent Publication No. 14092/72 (published on Apr. 27, 1972) discloses an oxidation reaction apparatus having the cross-sectional structure shown in FIG. 5 attached to the present application which is designed to perform the oxidation reaction of a p-dialkylbenzene smoothly by contacting the reactants with one another uniformly and rapidly in the reactor to afford terephthalic acid of high quality suitable for use in direct polymerization. This reaction apparatus comprises a reaction vessel 100, a gas exhaust port 106 at the top of the vessel, an opening 108 at the bottom of the vessel for withdrawing the oxidation product, an opening 105 at the bottom of the vessel for feeding a molecular oxygen-containing gas, a pipe 107 extending from the top to the bottom of the reaction vessel for refluxing condensed liquid, a hollow agitating shaft 102 within the vessel 100 having a hollow passage extending therethrough, a material supply opening 101 fitted to the top of the agitating shaft 102 leading to the hollow passage, and a plurality of hollow blades 103 secured to the shaft 102, each of said blades having a material feed opening 109 communicating with the hollow passage of the shaft 102. The apparatus is so designed that the starting p-dialkylbenzene is supplied from the opening 101, passed through the hollow passage within the shaft 102, and then introduced into the reactant mixture through the material feed openings 109 of the blades 103 while it is dispersed.

The apparatus of this Patent Publication is complex in structure and difficult to build because a continuous passage for feeding the material must be provided within the agitating shaft and the blades. In addition, the apparatus is difficult to operate stably over an extended period of time. Furthermore, the oxidative decomposition of the acetic acid solvent cannot be fully inhibited, and no reduction in power consumption can be expected.

Japanese Patent Publication No. 41624/76 (published on Nov. 11, 1976) suggests a process for producing terephthalic acid using an apparatus having the cross-sectional structure shown in FIG. 6 (the top portion is broken away) attached to the present application which is designed to produce high-purity terephthalic acid by improving the dispersion and mixing of the reactants in the reactor. This Patent Publication specifically discloses a process for producing terephthalic acid by the catalytic liquid-phase oxidation of p-xylene in a lower aliphatic carboxylic acid solvent using a reactor including an agitator which is equipped with multiple-stage impeller 3a, 3b, 3c, 3d, ... each having a diameter d and secured to a shaft at an interval l which is 1 to 1.5 times the impeller diameter d, wherein the starting p-xylene is fed into various parts of the reaction mixture through multiple supply tubes 2a, 2b, 2c, 2d, ..., and in order to achieve complete agitation, the reaction mixture is agitated with an agitating power of at least 9 HP/1000 gallons, preferably 9 to 100 HP/1000 gallons. In FIG. 6, the reference numeral 200 represents an opening for introducing a molecular oxygen-containing gas, and 201, an opening for withdrawing the oxidation reaction product. This apparatus, however, is complex in structure and difficult to build because a number of material feed pipes are provided within the reaction vessel. Moreover, it cannot fully inhibit the oxidative decomposition of the lower aliphatic carboxylic acid solvent, and a reduction in power consumption cannot be easily achieved because the agitator having flat blades is used in an attempt to achieve a completely agitated state.

Thus, all of these prior suggestions of avoiding the aforesaid disadvantages or troubles by improving the reaction apparatus are based on the technical idea of introducing the starting alkyl-substituted aromatic compound into the reaction system at a plurality of points, and no satisfactory result has been obtained from these suggestions.

The present inventors have made extensive investigations in order to avoid the aforesaid disadvantages and troubles by improving the reaction apparatus itself. These investigations have led to the discovery that the aforesaid disadvantages and troubles of the prior art can be overcome by departing from the technical idea of the prior art regarding the improvement of the apparatus for the liquid-phase catalytic oxidation reaction of alkyl-substituted aromatic compounds, and by designing the blades of an agitator such that they exert an action of agitating the reaction mixture within the reactor in a "combing" manner.

The present inventors specifically found that by providing an agitator having a plurality of blade stages at least one of which consists of comb-like flat blades each consisting of comb tooth-like pieces aligned at spaced intervals, there can be provided an improved apparatus for the liquid-phase catalytic oxidation reaction of alkyl-substituted aromatic compounds which can inhibit the undersirable oxidative decomposition of the lower aliphatic carboxylic acid solvent and consumes less power than the conventional apparatuses equipped with an agitator having flat blades, and which is simpler in structure and easier to build than the apparatuses based on the technical idea of the prior art.

It has also been found that this improved apparatus can be built advantageously by replacing only the flat agitating blades of the conventional apparatuses with the aforesaid unique comb-like flat blades in accordance with this invention.

A detailed mechanism by which the aforesaid improved effects can be obtained by using such comb-like flat blades has not yet been fully elucidated, but as shown hereinbelow by Example and Comparative Examples, the improved effects are outstanding. It is presumed from the above fact that in a reaction system in which an alkyl substituted aromatic compound is oxidized in the liquid phase with a molecular oxygen-containing gas in a lower aliphatic carboxylic acid solvent in the presence of an oxidation catalyst to form the corresponding aromatic carboxylic acid, the increase of the contact area between the reactant mixture and the molecular oxygen-containing gas, the increase of the efficiency of destroying the gas-liquid contacting boundary film, the maintenance of the reactivity of the gas-liquid contacting surface, and the uniform occurrence of these within the reaction mixture constitute important factors in overcoming the aforesaid disadvantages and troubles. The present inventors presume that according to the apparatus of this invention, these factors are conveniently satisfied, and the smooth, excellent and steady proceeding of the reaction can be secured, and the desired aromatic carboxylic acid of high quality can be formed without employing severe oxidation reaction conditions. It should be understood however that the present invention is in no way limited by the aforesaid theoretical analysis of the mechanism of this invention.

It is an object of this invention therefore to provide an apparatus for the liquid-phase catalytic oxidation of an alkyl-substituted aromatic compound with a molecular oxygen-containing gas, which can achieve the aforesaid improved results.

The above and other objects and advantages of this invention will become more apparent from the following description.

For facilitating understanding, the present invention is described in greater detail below with reference to the accompanying drawings in which.

Figure 1:
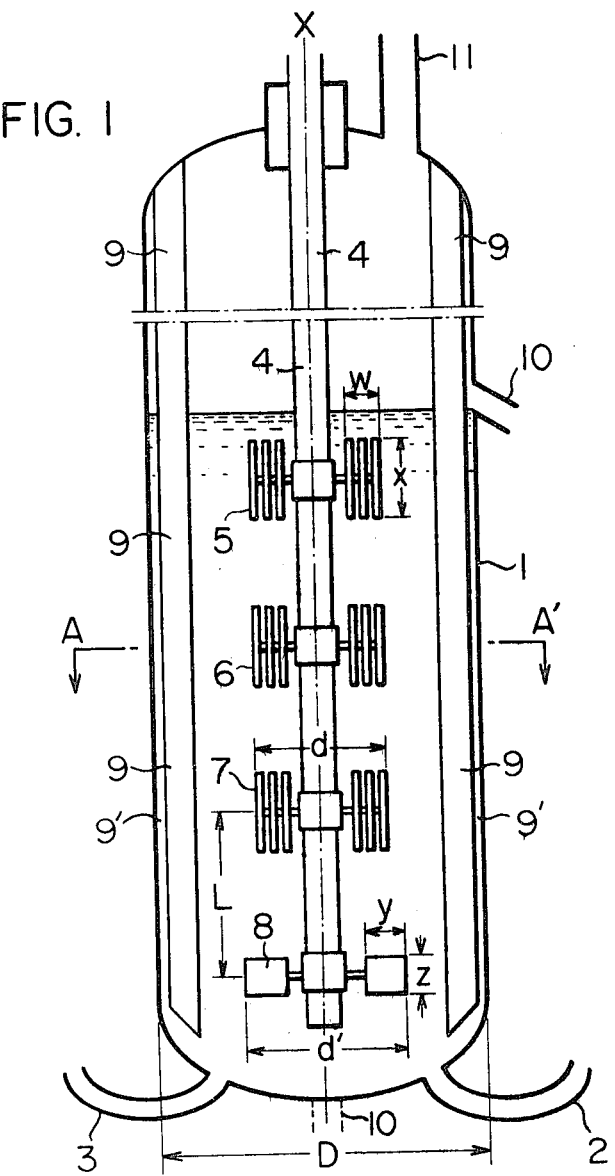
FIG. 1 is a schematic vertical sectional view of one example of the apparatus of this invention.
Figure 2:
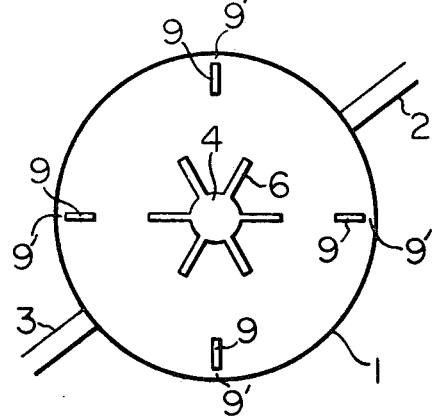
FIG. 2 is a schematic cross-sectional view taken along the line A-A' of FIG. 1.

In FIGS. 1 and 2, the reference numeral 1 represents a reaction vessel; 2, an inlet for feeding a molecular oxygen containing gas; 3, an inlet for feeding an alkyl-substituted aromatic compound as starting material; 4, a rotating shaft provided along the vertical axis X of the reaction vessel; 5, 6 and 7, comb-like flat blades each consisting of a plurality of comb tooth-like pieces aligned at spaced intervals; 8, conventional flat agitating blades; 9, a baffle plate; 10, an outlet for withdrawing the oxidation reaction product; and 11, a gas exhaust port.

In one embodiment of the apparatus of this invention shown in FIGS. 1 and 2, the material feed inlet 3 also serves as an inlet for feeding the lower aliphatic carboxylic acid solvent and the oxidation catalyst, and for example, the starting compound in the solvent containing the catalyst may be fed through the inlet 3. The solvent-feeding inlet and/or the catalyst-feeding inlet may be provided separately, for example at positions corresponding approximately to the middle of the liquid layer in the reactor. In this embodiment, the material feed inlet 3 is provided at the bottom of the reactor vessel 1, but it may be provided at other parts, for example at a position corresponding approximately to the middle of the liquid layer in the reactor.

The apparatus of this invention may also include a recycle inlet for recycling to the reaction system the solvent obtained by condensing the exhaust gas from the exhaust gas port 11, a recycle inlet for recycling the solvent forming the mother liquor of the product withdrawn from outlet 10 to the reaction system, and a feed inlet for recycling a part of the exhaust gas. If desired, two or more inlets may be provided at suitable positions to feed the molecular oxygen-containing gas, and the starting alkyl-substituted aromatic compound, respectively.

These changes in design can be easily chosen by those skilled in the art, and should be construed as included within the scope of the present invention.

In the embodiment shown in FIGS. 1 and 2, the apparatus of this invention comprises the reaction vessel 1, the gas exhaust port 11 at the top of the vessel 1, the molecular oxygen-gas feed inlet 2 at the bottom of the vessel 1, the starting material feed inlet 3 provided at the bottom of the vessel 1 and serving concurrently as an inlet for feeding the solvent and an inlet for feeding the oxidation catalyst, the outlet 10 for withdrawing the oxidation reaction product (in this embodiment, the outlet 10 is provided at a position corresponding to the upper part of the liquid layer within the vessel 1, but one or more of such outlets may be provided at positions corresponding to the middle and bottom portions as shown, for example, in FIG. 1 by dotted lines, of the liquid layer in the reactor vessel 1), and an agitator within the vessel, said agitator consisting of a rotating shaft provided along the axial direction of the vessel and a plurality of stages of agitating blades secured to said rotating shaft at spaced intervals; and is characterized in that at least one stage (in this embodiment, three stages out of four) consists of comb-like flat blades each of which is composed of a plurality of comb tooth-like pieces aligned at spaced intervals.

Figure 3:
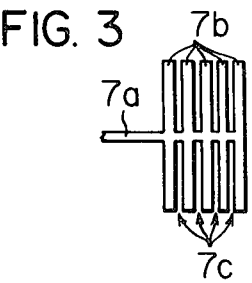
FIG. 3 is a top plan showing one example of agitating blade in the apparatus of this invention.
Figure 4:
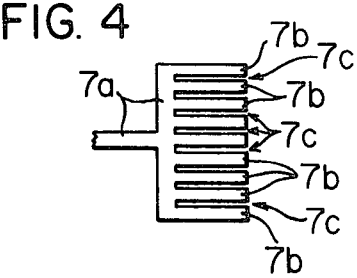
FIG. 4 is a top plan showing another example of agitating blade in the apparatus of this invention.
Figure 5:
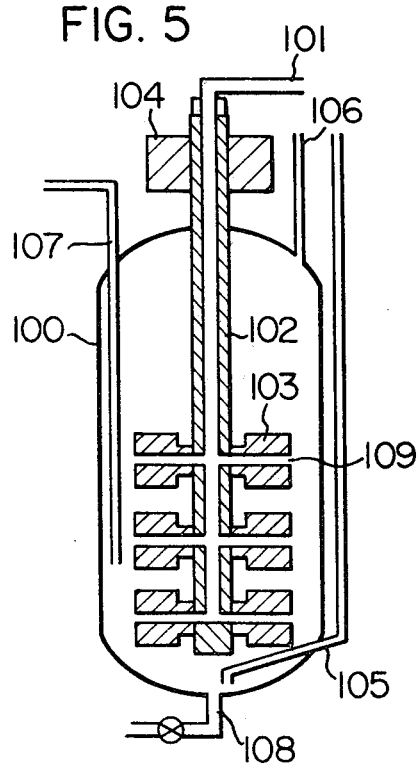
FIG. 5 is a schematic vertical sectional view of one example of the aforesaid conventional apparatus.
Figure 6:
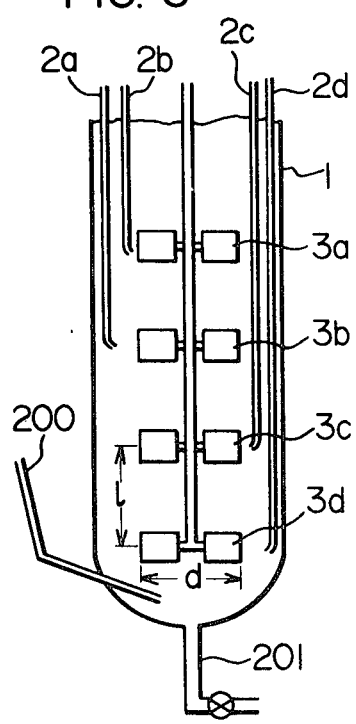
FIG. 6 is a schematic vertical sectional view (the top portion is broken away) of another example of the aforesaid conventional apparatus.

Examples of the comb-like flat agitating blade are illustrated in FIGS. 3 and 4. For example, in each comb-like flat blade 7, a plurality (5 in this embodiment) of comb tooth-like pieces 7b are secured to a rod-like arm 7a secured to the rotating shaft 4 (the securing portion is omitted) at spaced intervals 7c (4 intervals in this embodiment). Thus, as a whole, these pieces 7b form a comb-like flat blade. In another embodiment shown in FIG. 4, a plurality (9 in this embodiment) of comb tooth-like pieces 7b are secured to a T-shaped arm 7a fixed to the rotating shaft 4 (the securing portion is omitted) at spaced intervals 7c (8 intervals in this case) to form a comb-like flat blade as a whole. In these examples, the width of each comb tooth-like piece is approximately equal to the interval 7c, but if desired, the width of each comb tooth-like piece and/or each interval can be changed properly. Furthermore, in these examples, each comb tooth-like piece is rectangular in cross-section, but its shape may be changed to other shapes such as concavity, convexity, or a combination of these. As shown in FIG. 1, the length x of each comb-like flat blade in the direction of the rotating shaft 4 is preferably larger than its length w in a direction at right angles to the direction of the rotating shaft 4, for example w/x=about 1/5 to 1/1.5.

Preferably, the number of blade stages used in the apparatus of this invention is 2 or more, preferably 2 to about 8. Four stages are most preferred. The number of comb tooth-like pieces in each blade is preferably 2 to 8, and most frequently 4 to 6. In the embodiment shown in FIGS. 1 and 2, six agitating blades 6 are provided as shown in FIG. 2.

In the apparatus of this invention, all of the agitating blades may be the comb-like flat blades described hereinabove. It is also possible to combine such agitating blades with conventional flat blades. In particular, in the embodiment shown in FIGS. 1 and 2, the starting alkyl-substituted aromatic compound is introduced from the bottom of the reaction vessel, and the oxidation reaction product is withdrawn from the outlet provided at a position corresponding to the top of the liquid layer in the reaction vessel. Hence, the lowermost agitating blades 8 are preferably conventional flat blades 8. This embodiment is preferred because it strengthens the action of blowing the reaction mixture upward in the reaction vessel with agitation, and thus, sedimentation of the oxidation product to the bottom of the reaction vessel can be prevented. It is also possible to construct a plurality of blades in at least one stage from both conventional flat blades and the comb-like flat blades in accordance with this invention.

If a splash of the reaction mixture occurs at its surface and adheres to the inside surface of the reactor, terephthalic acid may precipitate and grow on it. Such a precipitate will fall into the reaction mixture at some time, and abruptly exert a great load on the agitating power, or clog the outlet for the withdrawal of the reaction product. To prevent this trouble, the uppermost stage may be made of conventional flat blades. If there is no such likelihood, it is preferred to use comb-like flat blades in all stages.

The agitating ability of the comb-like flat blades used in the apparatus of this invention will be reduced when their effective area of agitation becomes unreasonably small. Accordingly, in the examples shown in FIGS. 3 and 4, the width of comb tooth-like piece 7b is preferably larger than the interval 7c. The number of pieces 7b in each blade is usually 3 to 10, preferably about 3 to 6. The shapes of the pieces 7b shown in FIGS. 3 and 4 can be changed as desired, and incident to this, the shape of the interval 7c can also vary. Hence, in the apparatus of this invention, a suitable effective area of agitation can be conveniently shown by the number of times of the total area (P) of a plurality of comb tooth-like pieces in a comb-like flat blade (for example, the total of the areas of the pieces 7b in FIGS. 3 and 4) to the total area (Q) of the comb tooth-like intervals in the blade (for example, the total of the areas of the spaces 7c in FIGS. 3 and 4) when taken on a flat plane. In the apparatus of this invention, the total area (P) of the pieces 7b is preferably about 0.83 to about 3, more preferably about 1 to about 2, times the total area Q of the spaces 7c when taken on a flat plane.

The maximum diameter (d in FIG. 1) of a circle resulting from the rotation of the comb-like flat blade is preferably about 0.3 to about 0.7, more preferably about 0.3 to about 0.5, time the inside diameter (D in FIG. 1) of the reactor vessel. When a conventional flat blade such as the blades in the lowermost stage shown in FIG. 1 is used, the maximum diameter (d' in FIG. 1) of a circle resulting from the rotation of the flat blade is preferably about 0.3 to about 0.7, more preferably about 0.35 to about 0.6, time the inside diameter (D in FIG. 1) of the reaction vessel. In this case, the lengths expressed by y and z in FIG. 1 are preferably such that y/z is from about ½ to about 2/1.

The distance (L with regard to blades 7 and 8 in FIG. 1) between adjacent stages of blades (between blade stages 5 and 6, between blade stages 6 and 7, and between blade stages 7 and 8) is preferably about 0.6 to about 2 times, more preferably about 1 to about 1.5 times, the maximum diameter (in FIG. 1, d or d'; when d≠d', d+d'/2) of a circle resulting from the rotation of the blade.

In each unit of blades, the blade surfaces may be parallel to the direction of the rotating shaft, or be inclined in a direction crossing the direction of the rotating shaft. In the latter case, the surfaces of all the blades in each stage are preferably inclined in the same direction, and the angle of inclination formed between the blade surface and the rotating shaft is preferably less than about 30°. In the embodiment of FIG. 1 in which the blades 8 in the lowermost stage are conventional flat blades, these blades may have an angle of inclination of up to about 45°.

Preferably, the blades described hereinabove are designed such that the agitating power becomes 1 to 7 KW per m³ of the reaction mixture excluding any gaseous component.

Elongated rectangular baffle plates may be provided along the inner wall of the reaction vessel in a direction nearly parallel to the vertical axial direction of the reaction vessel at positions on the inner wall of the vessel or spaced from it by clearance 9' (see FIGS. 1 and 2) and away from the circumference of a circle resulting from the rotation of the agitating blades. In the embodiment shown in FIGS. 1 and 2, four baffle plates are provided as shown in FIG. 2. The number of such baffle plates is preferably from about 2 to about 6. The provision of such a baffle plate is advantageous in obtaining good mixing between the upper and lower portions of the reaction mixture, and the presence of the clearance 9' serves to prevent the deposit of the oxidation reaction product.

The apparatus of this invention has been developed in order to prepare an aromatic dicarboxylic acid by oxidizing an alkyl-substituted aromatic compound in the liquid phase with a molecular oxygen-containing gas in a lower aliphatic carboxylic acid solvent in the presence of an oxidation catalyst. This particular reaction is well known, and the excellent results described hereinabove can be achieved by performing the known reaction in the apparatus of this invention.

The following examples illustrate the present invention.

The 4-carboxybenzaldehyde (4-CBA for short) content of the resulting terephthalic acid was measured by polarography.

The light transmittance (%) of terephthalic acid was that of a 2 N aqueous solution of potassium hydroxide containing 15% by weight of the terephthalic acid which was measured at 340 m$\mu$.

The agitating power, or the power required for agitation, was determined by measuring the input by a wattmeter, and calculating the power which is substantially used for each stage volume of the reaction mixture excluding any gaseous component after taking into consideration the efficiency of the motor and the loss of the power.

The amount of acetic acid solvent consumed by oxidation was calculated from the concentrations of oxygen, carbon dioxide and carbon monoxide in the exhaust gas.

EXAMPLE 1

An apparatus of the type shown in FIG. 1 was used in which the impellers in the first, second and third stages were comb-like flat blades (d/D=0.4, L/(d+d'/2)=1.2, w/x=0.43, P=1.5Q) and the impellers in the lowermost stage were conventional flat blades (y/z=0.82).

A titanium-lined reactor 1 (capacity 0.63 m³) was charged with 420 kg of acetic acid, 30 kg of water, 3,350 g of cobalt acetate, 16.5 g of manganese acetate and 1,400 g of tetrabromoethane through feed inlet 3. The reactor was then maintained at a temperature of 180° C. and a pressure of 10 kg/cm², and a mixture consisting of p-xylene (110 kg/hr), acetic acid (420 kg/hr), water (30 kg/hr), cobalt acetate (3,350 g/hr), manganese acetate (16.5 g/hr) and tetrabromoethane (1,400 g/hr) was fed continuously into the reactor through feed inlet 3. In the meantime, air was fed continuously into the reactor through feed inlet 2 at a rate of about 4.9 Nm³/kg of p-xylene so that the oxygen concentration in the exhaust gas became 7%, and thus, p-xylene was oxidized continuously. The reaction product mixture was withdrawn from outlet 10 so that the residence time of the reaction mixture became 1 hour. The solid was separated by a solid-liquid separating technique, and washed thoroughly with acetic acid.

The resulting terephthalic acid had a light transmittance of 74% and a 4-CBA content of 700 ppm, and the power required for agitation was 1.6 kw/m³.

COMPARATIVE EXAMPLE 1

The procedure of Example 1 was repeated except that conventional flat blades (w/x=0.26) were also used in the first, second and third stages. The oxygen concentration of the exhaust gas was 7%. The agitating power required to obtain terephthalic acid having a light transmittance of 74% and a 4-CBA content of 700 ppm was measured.

COMPARATIVE EXAMPLE 2

The procedure of Comparative Example 1 was repeated by using an agitator having three stages of flat blades (d'/D=0.4, L/(d+d'/2)=1.2, w/x=0.75) as another example of conventional agitator.

The results of Example 1 and Comparative Examples 1 and 2 are shown in Table 1. The amount of acetic acid lost by decomposition is also shown.

| | Type of blades | O₂ concentration in the exhaust gas (%) | Amount of acetic acid lost(*) | Power consumed (kw/m³) |
|---|---|---|---|---|
| Example 1 | Three stages of comb-like flat blades and one stage of flat blades | 7 | 0.68 | 1.6 |
| Comparative Example 1 | Four stages of flat blades | 7 | 0.83 | 1.8 |
| Comparative Example 2 | Three stages of flat blades | 7 | 1.0 | 1.8 |

(*)The ratio to the amount in Comparative Example 2 which was taken as 1.0.

What we claim is:

1. In an apparatus for oxidizing an alkyl-substituted aromatic compound in the liquid phase with a molecular oxygen-containing gas in a lower aliphatic carboxylic acid solvent in the presence of an oxidation catalyst, said apparatus comprising a reaction vessel, a gas exhaust port at the top of the vessel, an inlet at the bottom of the vessel for feeding said molecular oxygen-containing gas, an inlet for feeding said solvent, an inlet for feeding said catalyst, an inlet for feeding said alkyl-substituted aromatic compound, an outlet for withdrawing the oxidation reaction product, and an agitator within the vessel, said agitator consisting of a rotating shaft provided along the axial direction of the vessel and a plurality of stages of agitating blades secured to said rotating shaft at spaced intervals; the improvement wherein at least one stage of the agitating blades consists of comb-like flat blades each of which is composed of a plurality of comb-like pieces aligned at spaced intervals; wherein the total area of said plurality of comb tooth-like pieces is about 0.83 to about 3 times the total area of the spaces among said comb tooth-like pieces in each comb-like flat blade when taken on a flat plane.

2. The apparatus of claim 1 wherein the number of said comb tooth-like pieces is 3 to 10 per blade.

3. The apparatus of claim 1 wherein the number of said comb-like flat blades is 2 to 8 per stage.

4. The apparatus of claim 1 wherein the number of said stages of agitating blades is 2 to 8.

5. The apparatus of claim 1 wherein the lowermost stage consists of flat blades having no comb-like structure.

6. The apparatus of claim 1 wherein the maximum diameter of a circle resulting from the rotation of each agitating blade is about 0.3 to about 0.7 time the inside diameter of said reaction vessel.

7. The apparatus of claim 5 wherein the maximum diameter of a circle resulting from the rotation of each flat blade is about 0.3 to about 0.7 time the inside diameter of the reaction vessel.

8. The apparatus of claim 1 wherein the distance between two adjacent agitator blade stages is about 0.6 to about 2 times the maximum diameter of a circle resulting from the rotation of said agitating blades.

9. The apparatus of claim 1 wherein 2 to 6 baffle plates are provided along the inner wall of said reaction vessel at least substantially parallel to the vertical axial direction of said vessel at positions on or away from said inner wall and away from the circumference of a circle resulting from the rotation of said agitating blades.

10. The apparatus of claim 1 wherein the comb-like flat blades comprise a rod-like arm secured to said rotating shaft perpendicularly thereto and a plurality of comb tooth-like pieces aligned parallel to each other and to said rotating shaft and secured to said rod-like arm at right angles thereto.

11. The apparatus of claim 1 wherein the comb-like flat blades comprise a T-shaped arm comprising a first leg secured to the rotating shaft perpendicularly thereto and a second leg perpendicular to and intersected by the first leg, and a plurality of comb tooth-like pieces aligned parallel to each other and to said first leg and secured to said second leg at right angles thereto.

* * * * *